United States Patent
Chung et al.

[11] Patent Number: 5,855,904
[45] Date of Patent: Jan. 5, 1999

[54] BIODEGRADABLE SUSTAINED RELEASE PREPARATION FOR TREATING PERIODONTITIS

[75] Inventors: Chong Pyoung Chung; Seung Jin Lee, both of Seoul, Rep. of Korea

[73] Assignee: Dong Kook Pharmaceutical Co., Ltd., Seoul, Rep. of Korea

[21] Appl. No.: 817,552

[22] PCT Filed: Oct. 16, 1995

[86] PCT No.: PCT/KR95/00132

§ 371 Date: Apr. 3, 1997

§ 102(e) Date: Apr. 3, 1997

[87] PCT Pub. No.: WO96/13253

PCT Pub. Date: May 9, 1996

[30] Foreign Application Priority Data

Nov. 1, 1994 [KR] Rep. of Korea .................. 1994-28496

[51] Int. Cl.$^6$ ...................................... A61F 2/00
[52] U.S. Cl. .................... 424/426; 424/423; 424/424
[58] Field of Search .............. 424/426, 422–424

[56] References Cited

U.S. PATENT DOCUMENTS

| | | | |
|---|---|---|---|
| 2,667,443 | 1/1954 | Ashton | 167/93 |
| 2,748,781 | 6/1956 | Collat | 132/93 |
| 3,219,527 | 11/1965 | Gurney | 167/60 |
| 3,339,546 | 9/1967 | Chen | 128/156 |
| 3,417,179 | 12/1968 | Roth | 424/28 |
| 3,679,360 | 7/1972 | Rubin | 23/109 |
| 3,698,392 | 10/1972 | Vogt | 128/268 |
| 3,844,286 | 10/1974 | Cowen | 128/260 |
| 3,911,099 | 10/1975 | DeFoney | 428/28 |
| 3,942,539 | 3/1976 | Corliss | 132/79 E |
| 3,964,164 | 6/1976 | Hesselgren | 32/1 |
| 3,991,766 | 11/1976 | Schmitt | 128/335.5 |
| 4,020,558 | 5/1977 | Cournut | 32/40 R |
| 4,175,326 | 11/1979 | Goodson | 433/80 |
| 4,744,933 | 5/1988 | Rha et al. | 264/4.3 |
| 4,942,129 | 7/1990 | Goosen et al. | 435/182 |
| 4,965,262 | 10/1990 | Kametaka et al. | 514/230.2 |

FOREIGN PATENT DOCUMENTS

| | | |
|---|---|---|
| 0 451 390 | 10/1991 | European Pat. Off. . |
| 92/00718 | 1/1992 | WIPO . |

Primary Examiner—Thurman K. Page
Assistant Examiner—Kathryne E. Shelborne
Attorney, Agent, or Firm—Merchant, Gould, Smith, Edell, Welter & Schmidt

[57] ABSTRACT

The present invention relates to a biodegradable sustained release preparation for treating periodontitis, especially containing polysaccharide. The core of the preparation according to the present invention consists of medicine and polysaccharide, i.e. sodium alignate, and is coated with cationic chitosan. By the function of chitosan building the coating of the preparation, the medicine is slowly released, and the carrier is completely decomposed by lysozyme in vivo after the release of the medicine.

3 Claims, 3 Drawing Sheets

BIODEGRADABLE SUSTAINED RELEASE PREPARATION FOR TREATING PERIODONTITIS

This application is a 371 of PCT/KR95/00132 filed Oct. 16, 1995.

BACKGROUND OF THE INVENTION

1. Field of the Invention

The present invention relates to a biodegradable sustained release preparation for treating periodontitis. More specifically, this invention relates to a biodegradable sustained release preparation for treating periodontitis characterized in that the core, which is further coated with chitosan, of the preparation contains medicine and polysaccharide, i.e. sodium alginate.

Periodontitis, an inflammation of periodontium caused by anaerobic bacteria, is a periodontal disease exacerbated from gingivitis. Because periodontitis destructs collagen supporting alveolodental membrane and dissolves alveoru, periodontal ligament are dissociated and periodontal cyst, an important clinical symptom, is invaded. In serious symptom, teeth are lost. The pathogenetic bacteria causing periodontitis are mostly gram-negative anaerobic bacteria. Those bacteria destruct desmoplasm and periodontal ligament of alveolodental membrane a side effect of migrating polymorphonuclear cell depravates inflammation.

2. Description of the Prior Art

The general therapy of periodontitis in the prior art includes apparatotherapy such as scaling, curettage or root planing. However, these therapies are used only as a supplementary method due to high recurrens. Therefore, in order to treat periodontitis, pharmacotherapy have to be used primarily.

Examples of pharmacotherapy includes antibiotic therapy for controlling gram-anaerobic bacteria and therapy of using antiphlogistic for laxation of inflammation. Among the various antibiotics, tetracycline-type medicines are preferred because they are used widely and have low toxicity for human beings. Since the MIC (minimum inhibition concentration) 90% value is 8 $\mu$g/ml, the effectiveness of these medicines is high enough to be maintained for 6 months per only a dose.

With regard to antibiotic therapy, in case of systemic medication, since an excessive amount of antibiotics have to be used for maintaining the effective concentration of medicine in the palatal bursa of gingiva, the side effect and manifestation of tolerance are occurred.

Alternatively, in case of the generally preferred topical therapy, oral irrigation is preferred in order to administrate the antibiotics topically. However, this therapy is unsuitable because the medicine can not satisfactorily pass through periodontal cyst. Also, a method of direct injection of medicine with a syringe is only effective for a short-term-therapy but not for a long-term therapy.

In these circumstances, a sustained release preparation which can slowly release medicine in periodontal cyst by inserting a carrier into periodontal cyst has been recently developed in order to solve these problems.

This method has been disclosed in the documents as follows: U.S. Pat. No. 3,911,099 capsules and tablets of prolonged effects; U.S. Pat. No. 4,020,518 a buccal implant of which medicine is released by saliva; U.S. Pat. No. 3,679,360 topical gel; U.S. Pat. No. 3,339,546 bandages containing topical medicine; U.S. Pat. No. 3,964,164 plastic mass containing medicine; U.S. Pat. No. 3,219,527 medicated periodontal dressing; U.S. Pat. No. 3,698,392 topical dressing containing medicine dispersed in microparticulated carrier; U.S. Pat. No. 4,329,333 droplet of medicine microcapsulated; and U.S. Pat. No. 3,844,286 foam film devices containing medicine.

While collagen film containing tetracycline developed by Minabe etc., is a biodegradalde preparation of which effective concentration is prolonged over 10 days in palatal bursa of gingive, it has a disadvantage of causing immunoreaction due to hetero antigen-protein.

While filamentous devices containing medicine, described in U.S. Pat. No. 3,417,179, U.S. Pat. No. 2,667,443, U.S. Pat. No. 2,748,781 and U.S. Pat. No. 3,942,539 and hollow fiber device described in U.S. Pat. No. 4,175,326, both made of cellulose acetate, are effective in inclusion of medicine but not in control of releasing medicine.

In case of hollow fiber, the. elution of 95% of medicine is completed in 2 hours, while in case of monolith fiber, that is completed in one day. Also, monolith fiber made of ethylene vinyl acetate polymer is excellent as a sustained release preparation because the elution of medicine is prolonged for 9 days.

However, since the carrier is insoluble so that it can react as a physical promoter in inflammation reaction, and it should be removed after treatment due to its undegradability, they are disadvantageous to be used.

As a filamentous biodegradable medicine, polyglycolic acid fiber containing medicine is described in U.S. Pat. No. 3,991,766. Besides, there is soluble hydroxypropyl cellulose strip, as a soluble carrier, developed by Niguchi. Although there is not disadvantage of removing after treatment because of its high solubility, it is unsuitable for long-term therapy since the elusion of medicine is completed in 24 hours due to dissolution of carrier. Further, hydrophilic paste preparation to be injected to periodontal cyst with syringe containing tetracycline has been developed. However, the dependency between the clinical effect and change in concentration of tetracycline has not yet been determined.

SUMMARY OF THE INVENTION

Therefore, in order to solve the above described problems, the present invention has an object to provide an advanced biodegradable sustained release medicine carrier.

To attain the object described above, this invention provides a biodegradable sustained release preparation of which the core contains sodium alginate unit and medicine, and the surface thereof is coated with chitosan. Accordingly, the preparation of the present invention can maximize the inclusion effect of medicine into periodontal cyst and slowly release the medicine for a prescribed period by preparing microcapsules with polysaccharide.

DESCRIPTION OF THE PREFERRED EMBODIMENT

Figure 1:
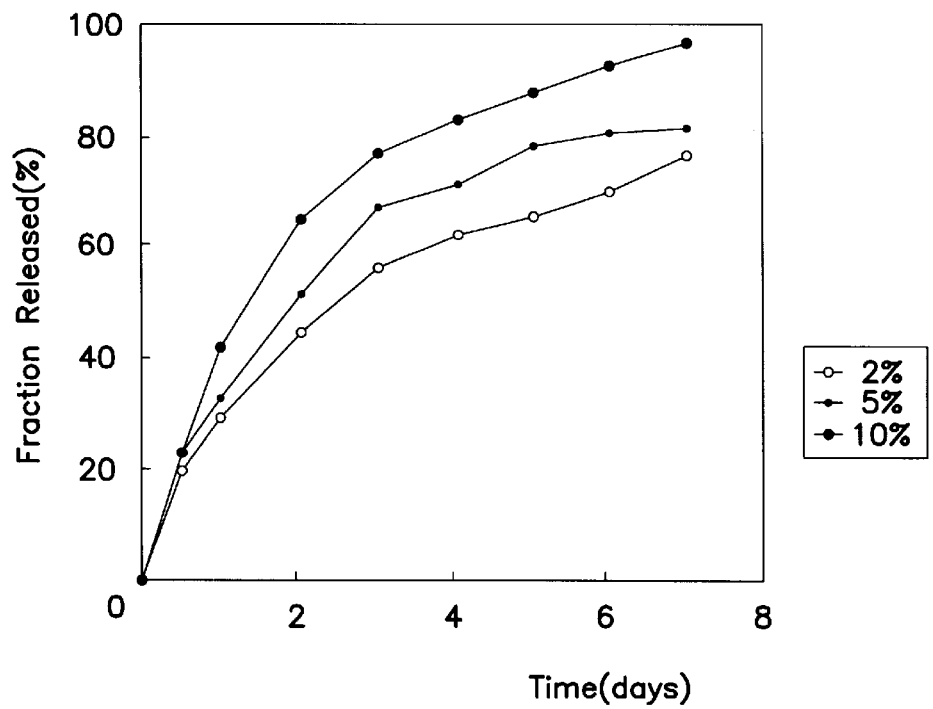
FIG. 1 is a graph showing the releasing pattern of medicine dependent upon content of medicine of Example 1.

Polysaccaride is non-toxic, nonimmunological and natural polymer, and attempts of using this polymer as a pharmaceutical carrier have been recently tried. Since it can be dissolved in vivo and degraded by hydrolysis or enzyme, it is excellent biodegradable material having a great possibility of being used as a graft.

Therefore, the present inventors prepared anionic polysaccaride microspheres containing medicine by using gelating power of polysaccaride and then coating thereof with a cationic polymer, i.e. chitosan to provide microcapsules.

At first, microspheres are prepared by gelation of a solution of sodium alginate with bivalent cation. Then, the product is reacted with cationic polymer of chitosan, of which ionic character is counter to alginic acid, to form a film to make microcapsules.

The elution of medicine of the preparation produced by the present method is controlled by film of chitosan. After releasing medicine, chitosan is dissociated by enzyme in mouth such as lysozyme. The role of polysaccharide, i.e. sodium alginate as a unit of preparation is inclusion of medicine into the preparation, and the role of chitosan is controlling the release of medicine.

The concentration of chitosan is about 2% by weight/volume. If the concentration is far lower than 2% by weight/volume, it is impossible to control the release of medicine for 7 days, where the effect of the coated layer decreases by viscous chitosan if the concentration is far higher than 2% by weight/volume.

The size of the microparticle containing medicine is desirably about 70 µm. If the size is far larger than 70 µm, injection from a container for applying the preparation into periodontal cyst is difficult, where the medicine releases in short period if the size is far smaller than 70 µm.

The medicine used in the preparation of the present invention includes tetracycline hydrochloride, tetracycline bases, minocycline hydrochloride, ibuprofen or flubiprofen, and, in particular, minocycline hydrochloride is desirable. The content of the above medicine is preferably 2% to 10% by weight each with respect to the weight of the final formulation. If the content is lower than 2% by weight, it is impossible to maintain the released concentration of medicine to MIC, where the medicine may cause toxicity if the content exceeds 10% by weight.

The present invention is illustrated in further detail by way of following examples, and it is to be understood that modifications of the present invention will be no doubt apparent to a person having ordinary skill in the art to which the invention pertains, within the spirit and scope of the present invention.

EXAMPLE 1

A 2% by weight/volume solution of sodium alginate containing medicine was added dropwise to a 1.5% by weight/volume aqueous solution of calcium chloride by using a droplet extruser nozzle through which a compressed gas was passing. After dropping, the mixture was gellated for 5 minutes. Subsequent to washing and filtering the resultant gelated particles, collected microparticles were coated with 2% by weight/volume solution of chitosan for 10 minutes.

The medicine was minocycline hydrochloride, and the content of the above medicine was 2%, 5% or 10% by weight each with respect to the weight of the final formulations.

The experiment of releasing the medicine from the microspheres prepared was carried out by the following steps: 50 mg of microspheres put in a basket was added to 50 ml of HEPES buffer solution and the resultant mixture was shaked at 37°±0.5° C. 15 rpm; the samples were collected in a predetermined duration for 7 days and quantatively analysed by the use of UV spectrophotometer.

The result is shown in FIG. 1. This graph shows the release pattern where the content of medicine was 2%, 5% or 10% by weight/volume each. It is found that the release of the medicine increases proportionally to the content of medicine. The initial rate of release increased with the increase of medicine content, and then the release of medicine increased with constant rate.

EXAMPLE 2

Coated microspheres were prepared in accordance with Example 1 but a 2% by weight/volume solution of sodium alginate without containing medicine. The coated microsperes were then immersed in a medicinal solution, and it was left alone for 24 hours and dried to make the content of medicine with respect to the final formulation become 2%, 5% or 10% by weight.

Figure 2:
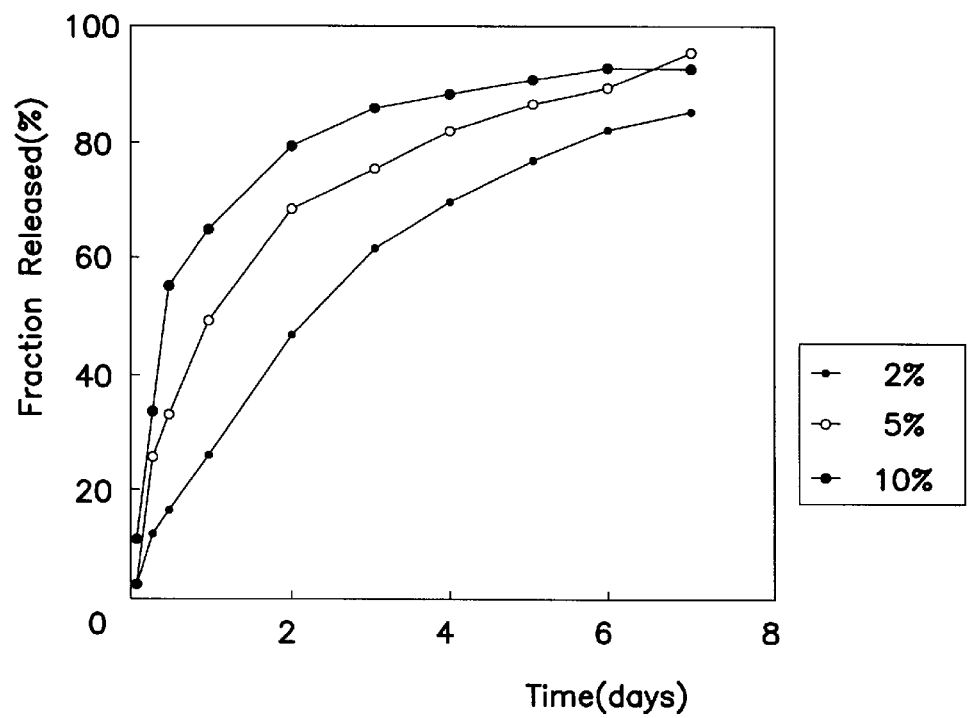
FIG. 2 is a graph showing the releasing pattern of medicine dependent upon content of medicine of Example 2.

The result of experiment for the release of medicine is shown in FIG. 2.

EXAMPLE 3

Microspheres prepared in Example 2 were immersed in 0.5%, 1% or 2% by weight/volume solution of minocycline hydrochloride respectively so that the swelling load was carried out. The content of the medicine was made 2%, 5% or 10% by weight each with respect to the weight of the final formulation, dependent upon the concentration.

The time period for swelling load was 24 hours. Then, the microparticles encapsulating medicine was coated with a 2% by weight/volume solution of chitosan.

Figure 3:
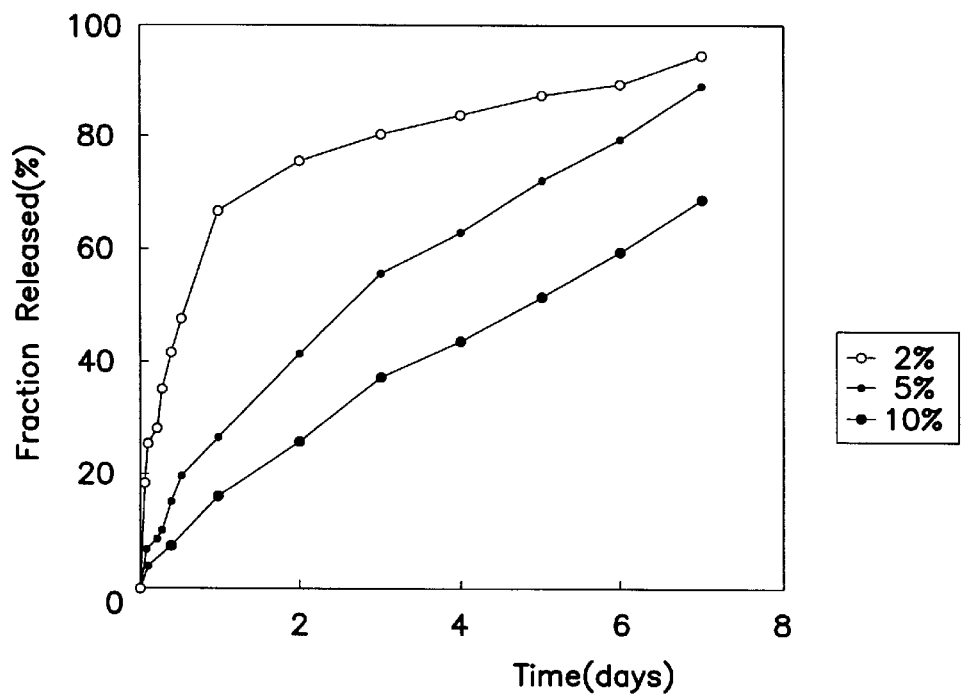
FIG. 3 is a graph showing the releasing pattern of medicine dependent upon content of medicine of Example 3.

The result of experiment for the release of medicine is shown in FIG. 3.

EXAMPLE 4

A solution of sodium alginate containing medicine was emulsion-dispersed in organic solvent containing a surfactant. To the resultant dispersion was added dropwise a solution of calcium chloride so that microparticles of gel was formed. The organic solvent was a 3:1 mixture of hexane and chloroform, and the surfactant used was Span, a surfactant of sorbitan monostearate. The concentration of the surfactant was 0.4% by weight/volume with respect to the dispersion medium. The resultant microparticles were collected, washed and filtered. Then a 2% by weight/volume solution of chitosan was added thereto to form a coating.

The medicine was minocycline hydrochloride and the content of the above medicine was 2%, 5% or 10% by weight each with respect to the weight of the final formulation.

Figure 4:
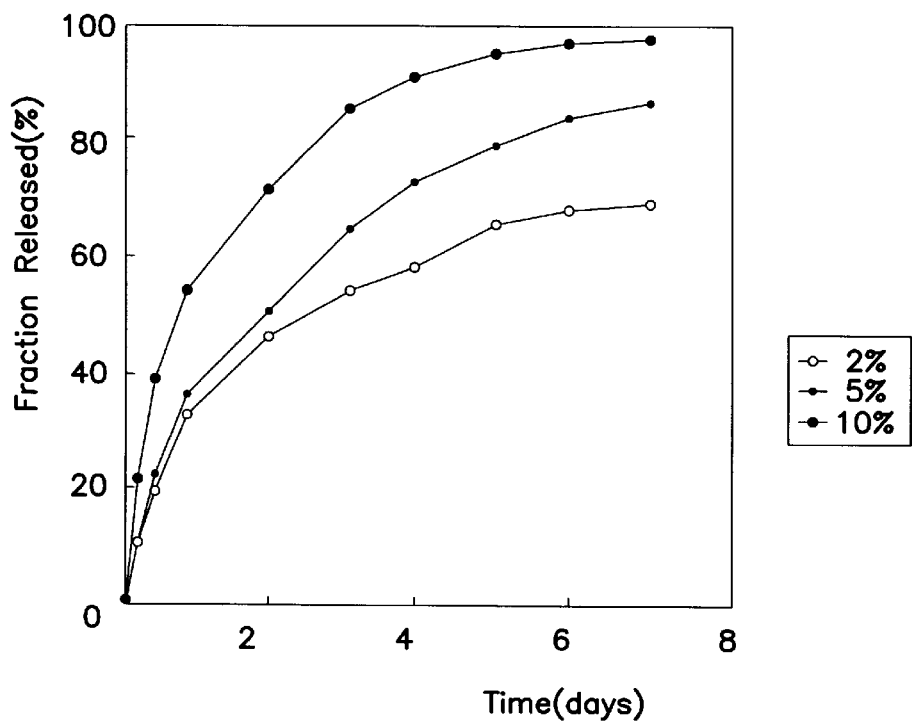
FIG. 4 is a graph showing the releasing pattern of medicine dependent upon content of medicine of Example 4.

The result of the experiment for release of medicine is shown in FIG. 4.

EXAMPLE 5

According to Example 4, microparticles of sodium alginate without containing medicine were prepared and these were immersed in each medicinal solutions with different concentration to be swelling loaded.

The medicine was minocycline hydrochloride and each content of the above medicine was 2%, 5% or 10% by weight with respect to the weight of the final formulations. The time period for swelling load was 24 hours. After washing and filtering, the microparticles encapsulating the medicine were coated with a 2% by weight/volume solution of chitosan.

Figure 5:
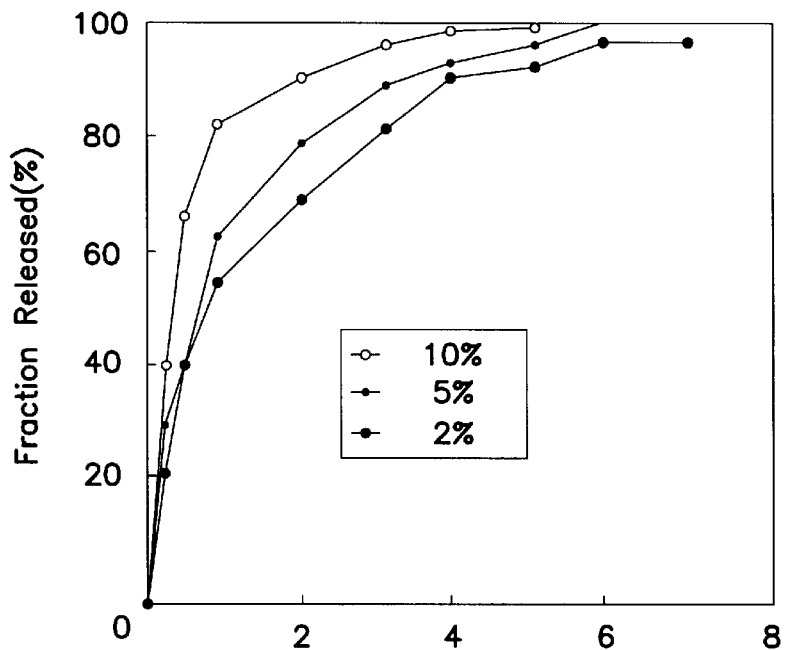
FIG. 5 is a graph showing the releasing pattern of medicine dependent upon content of medicine of Example 5.

The result of the experiment for release of medicine is shown in FIG. 5.

Figure 6:
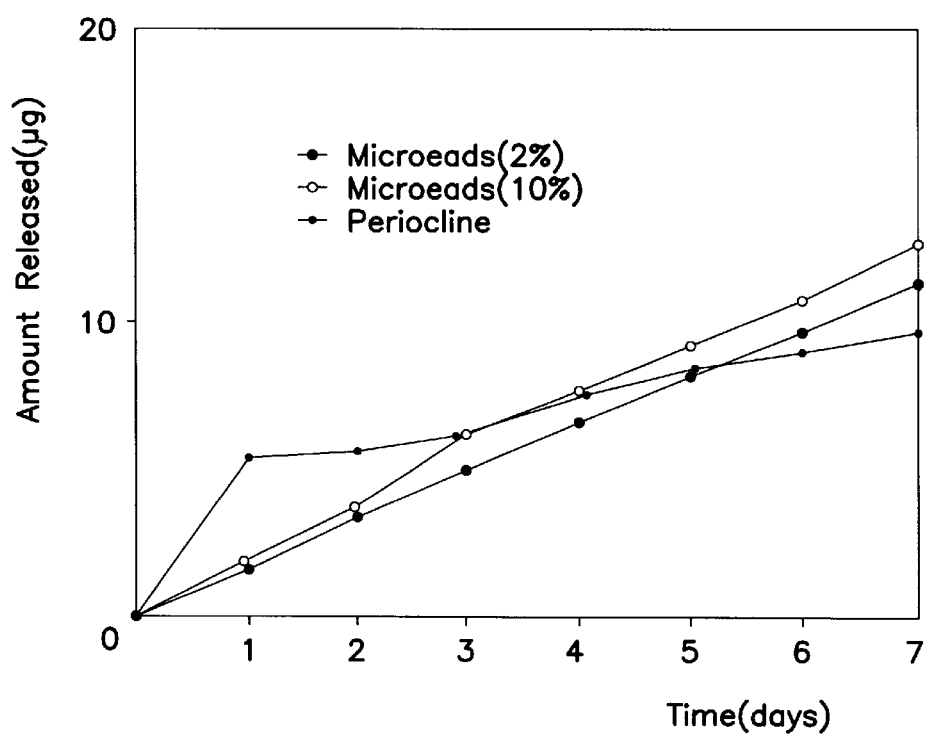
FIG. 6 is a graph showing the comparison of release of medicine from the biodegradable sustained release preparation in accordance with the present invention to the release from a conventional product, Periocline.

As can be seen from the result of the experiment for release of medicine for 7 days, where the conventional product, Periocline shows maximum release rate in first day and the increase of release was extremely weak thereafter, the biodegradable sustained release preparation according to the present invention shows gradual increase of releasing rate from the period after first day to the seventh day (See FIG. 6).

Therefore, the present invention provides a biodegradable sustained release preparation which can slowly release the antibiotic in periodontal cyst in a long-term period.

What is claimed is:

1. A method for preparing a biodegradable sustained release preparation for external use for treating periodontitis, comprising the steps of:

gelating sodium alginate solution without active ingredient with calcium chloride solution;

forming a capsulated microsphere by capsulating it with chitosan solution by ionic reaction between an anion thereof and a cation of said chitosan; and swelling the capsulated microsphere in a solution containing at least one active ingredient selected from the group consisting of tetracycline hydrochloride, tetracycline bases, minocycline hydrochloride, ibuprofen or flubiprofen.

2. The method of claim 1, further including the step of drying the capsulated microsphere.

3. The method of claim 2, wherein the step of drying the capsulated microsphere includes providing the biodegradable sustained release preparation with a content by weight of the active ingredient ranging from about 2–10%.

* * * * *